United States Patent [19]

Eckel

[11] Patent Number: 5,768,723
[45] Date of Patent: Jun. 23, 1998

[54] AUDIOMETRIC CRIB FOR INFANTS

[76] Inventor: Alan Eckel, 10 Hildreth St., Westford, Mass. 01886

[21] Appl. No.: 650,979

[22] Filed: May 21, 1996

[51] Int. Cl.⁶ .................................................. A61B 5/12
[52] U.S. Cl. .................................. 5/93.1; 5/97; 128/746; 600/21
[58] Field of Search ................................ 5/93.1, 97, 423, 5/284, 655; 600/21, 22; 128/746; 49/169, 171, 386, 381; 454/56, 254, 271, 276, 906; 220/377, 602, 663, 661, 676, 373, 745, 335; 312/138.1, 139; 52/171.1, 204.62, 204.67, 656.5

[56] References Cited

U.S. PATENT DOCUMENTS

| | | | |
|---|---|---|---|
| 413,544 | 10/1889 | Peace et al. | 220/335 |
| 1,242,545 | 10/1917 | Hanger, Sr. | 5/97 |
| 2,369,396 | 2/1945 | Higginbotham | 600/22 |
| 2,417,962 | 3/1947 | Armstrong | 600/22 |
| 2,700,384 | 1/1955 | Ivory | 600/21 |
| 3,240,375 | 3/1966 | Burrows | 220/335 |
| 3,611,907 | 10/1971 | Wasserman | 98/33 |
| 3,789,747 | 2/1974 | Wasserman et al. | 98/33 |
| 3,833,964 | 9/1974 | Harcourt | 220/335 |
| 3,969,857 | 7/1976 | Stark | 52/656.5 |
| 4,042,199 | 8/1977 | Winkler | 5/310 |
| 4,163,875 | 8/1979 | Cogan | 179/103 |
| 4,213,536 | 7/1980 | Hafner | 220/663 |
| 4,325,492 | 4/1982 | Kunze | 220/335 |
| 4,416,094 | 11/1983 | Bügener et al. | 49/386 |
| 4,750,474 | 6/1988 | Dukhan et al. | 128/113 |
| 4,846,783 | 7/1989 | Koch et al. | 600/22 |
| 4,899,420 | 2/1990 | Bye et al. | 49/386 |
| 4,936,824 | 6/1990 | Koch et al. | 600/22 |
| 5,123,874 | 6/1992 | White, III | 52/582.2 |
| 5,285,519 | 2/1994 | Barsky et al. | 392/439 |

*Primary Examiner*—Steven N. Meyers
*Assistant Examiner*—Robert G. Santos
*Attorney, Agent, or Firm*—Pandiscio & Pandiscio

[57] ABSTRACT

An audiometric crib for infants includes a housing having a floor and walls upstanding from the floor, and a door connected to the housing and adapted to move between an open position for moving an infant into and out of the housing and a closed position for isolating the infant from ambient noise and for conducting auditory tests on the infant. Ventilators are provided for directing air into the housing and exhausting air from the housing. Means are provided in one or more of the walls for accommodating in an air-tight manner a transmission line for introducing controlled acoustic signals from outside the crib to the infant in the crib, and for carrying signals from a sensor on the infant in the crib to instrumentation outside of the crib.

2 Claims, 4 Drawing Sheets

AUDIOMETRIC CRIB FOR INFANTS

BACKGROUND OF THE INVENTION

1. Field of the Invention

The invention relates to audiometric enclosures and is directed more particularly to an audiometric booth or crib suitable for infants.

2. Description of the Prior Art

It is known to provide sound proof chambers for testing of hearing of persons. Such chambers are known as audiometric booths and are typically somewhat akin to telephone booths in configuration, providing room for a patient to stand or sit and undergo tests, such as pushing buttons in response to perceived acoustical tones directed through earphones, or the like. The chamber reduces the ambient noise to which the patient otherwise would be subjected.

Of late, it has become clear that many problems relative to learning disabilities, or shortcomings, in young school children, stem from hearing deficiencies which go undetected, it being often assumed that the problem is one of inattentiveness or lack of intelligence, or the like. On occasion, the problem is detected but not until well after the start of the educational process, leaving a weak educational underpinning for school years yet to come.

Having recognized the problem, it is becoming accepted that children in infancy should be tested for hearing impairments. In some areas of the U.S., such testing has become mandatory. Unfortunately, the audiometric booths used by most health providers are not suitable for infants.

Accordingly, there is a need for an audiometric booth which accommodates infants and in which an infant may be tested for hearing deficiencies.

SUMMARY OF THE INVENTION

An object of the invention is to provide an audiometric enclosure in the form of a crib into which infants may easily be placed and remain safe and comfortable during a hearing examination.

With the above and other objects in view, as will hereinafter appear, a feature of the present invention is the provision of an audiometric crib for infants, the crib including a housing having a floor and walls upstanding from the floor, and a door connected to the housing and adapted to move between an open position for moving an infant into and out of the housing, and a closed position for isolating the infant from ambient noise and for conducting auditory tests on the infant. Ventilation means are provided for directing fresh air into the housing and exhausting air from the housing. A conduit is provided in the walls for retaining in an air-tight manner a transmission line for introducing controlled acoustic signals from outside the crib to the infant in the crib, and for carrying signals from a sensor on the infant in the crib to instrumentation outside of the crib.

The above and other features of the invention, including various novel details of construction and combinations of parts, will now be more particularly described with reference to the accompanying drawings. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention, from which its novel features and advantages will be apparent.

In the drawings.

DESCRIPTION OF THE PREFERRED EMBODIMENT

Figure 2:
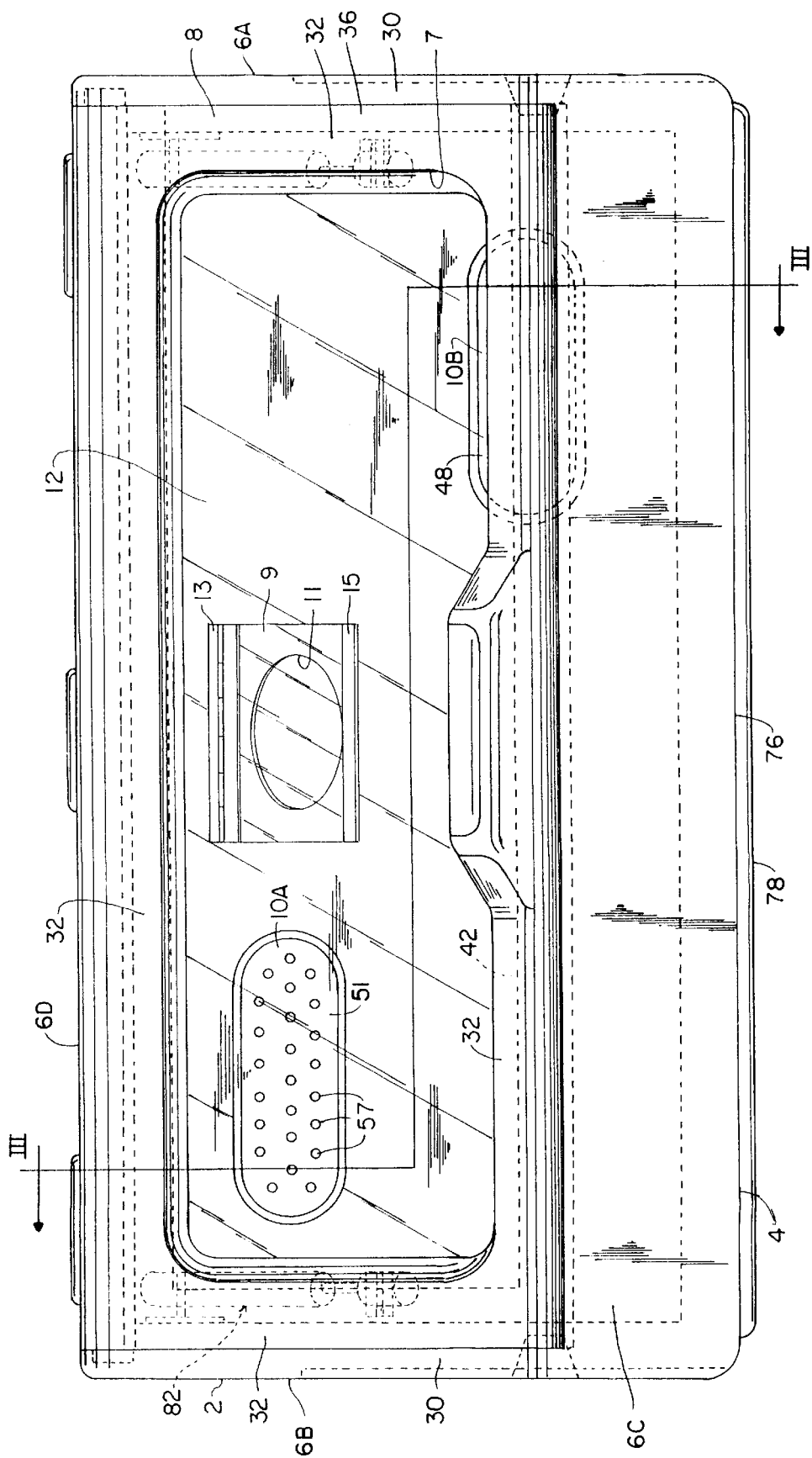
FIG. 2 is a front elevational view of the crib of FIG. 1.

Referring to the drawings, it will be seen that an illustrative embodiment of the invention includes a housing 2 having a floor 4 for supporting a prostrate infant, and walls 6 (A–D) upstanding from the floor 4. Walls 6 are designated as left and right side walls 6A and 6B (as seen in FIG. 2), front wall 6C, and rear wall 6D. A door 8 is hingedly connected to the housing 2 and is adapted for movement between an open position (shown in phantom in FIG. 3) for moving an infant into and out of the housing 2, and a closed position (shown in solid lines in FIG. 3) for isolating the infant from ambient noise and for conducting auditory tests on the infant.

The hinge means are not shown in detail, since various forms of hinge constructions may be used to pivotally mount door 8 to housing 2. Preferably door 8 is formed with lateral projections or pivot pins 92 on each end that are rotatably received in the aforementioned side walls of the housing.

Housing 2 and door 8 are formed as hollow dual partition members. This is accomplished by rotational molding using a suitable plastic molding material, preferably a linear low density polyethylene. A low density polyethylene is preferred since it is more compliant to external pressures and, therefore, is capable of better sound attenuation and isolation than a housing and door made of a high density, less flexible material, particularly if the housing and door are single partition structures.

The crib is provided with ventilation means 10A, 10B (FIGS. 2 and 3) for directing air into the housing 2 and exhausting air from the housing, when the door 8 is in the closed position.

Figure 1:
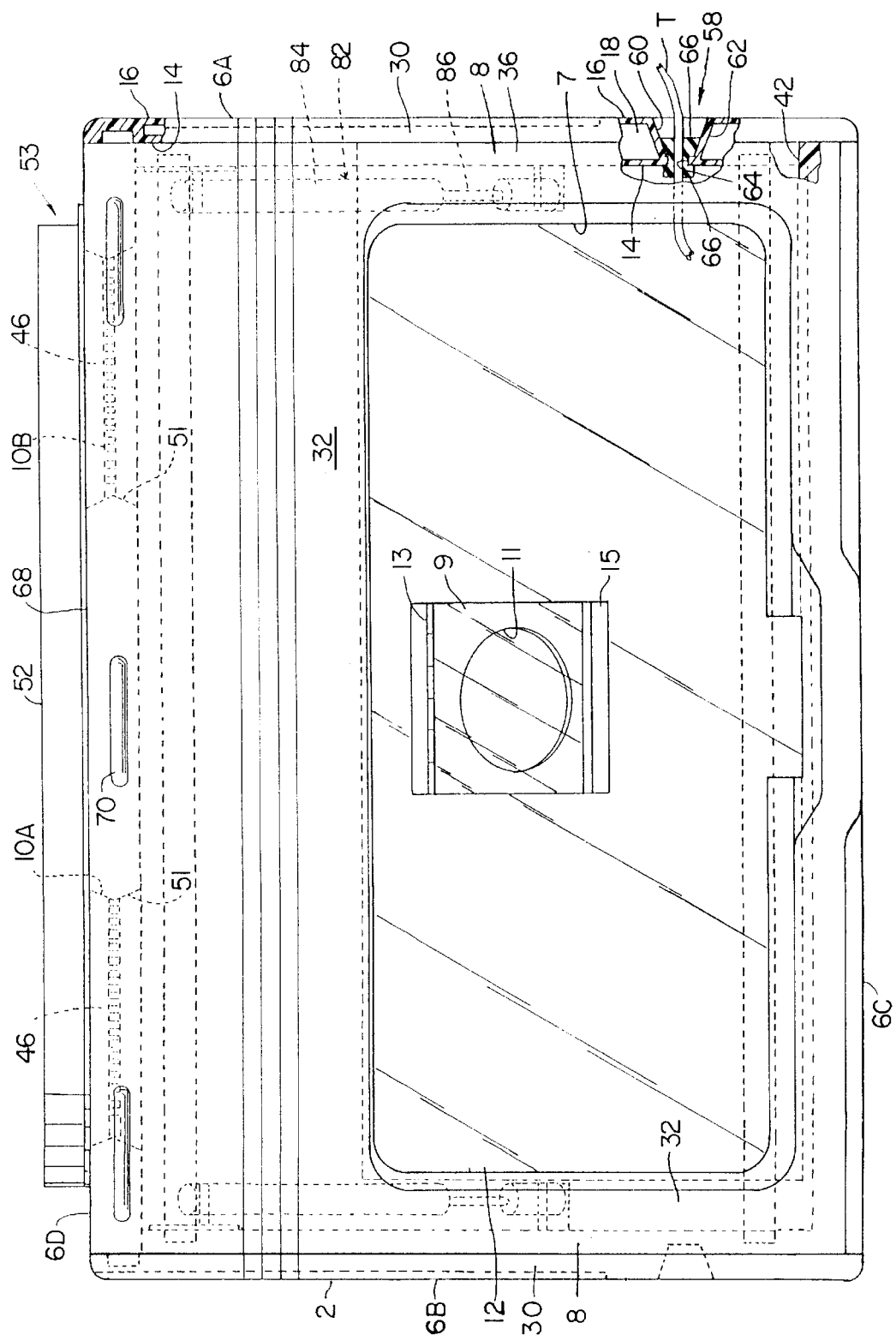
FIG. 1 is a top plan view, with portions broken away, of one form of audiometric crib illustrative of an embodiment of the invention.

As shown in FIGS. 1 and 2, the door 8 is provided with a window opening 7 that is closed off by a transparent window pane 12. The door 8 may be provided with a smaller hatch 9 hingedly mounted on the window pane 12, the window pane 12 having an opening 11 therein underlying the hatch 9. The hatch 9 and window pane 12 preferably are of a rigid translucent plastic material, enabling mounting of a hatch hinge 13 on the window pane 12 by adhesive, screws, or other suitable fastening means. The hatch 9 preferably is provided with a handle portion 15. Thus, for quick adjustments inside the closed crib, an attendant may simply flip open the hatch 9 and extend an arm into the crib by way of the opening 11, without having to hoist open the larger door 8. The window opening 7 is positioned so that the infant may be viewed from positions in front of, and over, the crib, enabling attending medical personnel to keep an eye on the infant while adjusting related instrumentation or pursuing other tasks, and not having to peer down into the housing to observe the infant therein.

Figure 3:
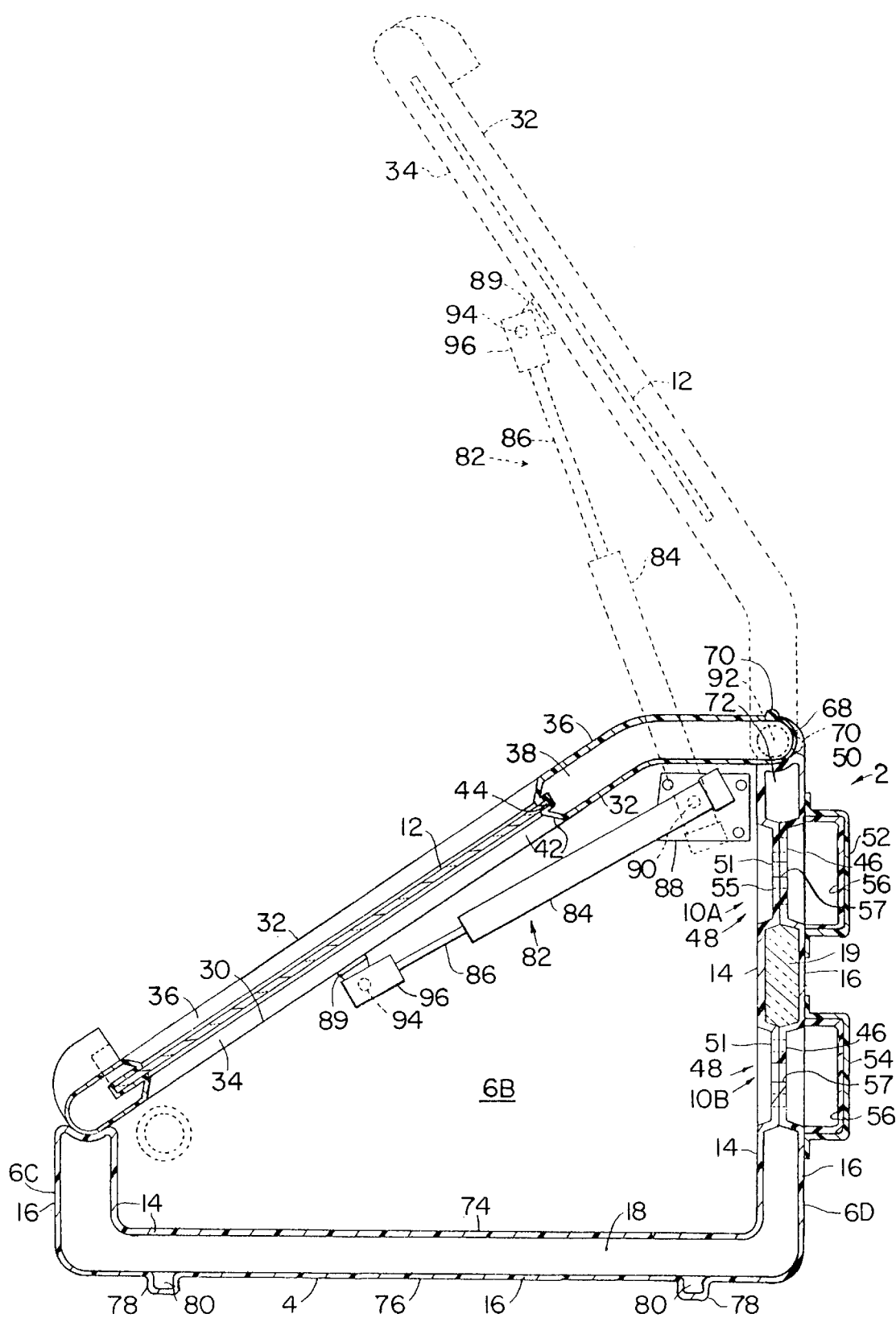
FIG. 3 is a sectional view taken along line III—III of FIG. 2.

The side walls 6A, 6B are formed integral with floor 4, front wall 6C, and back wall 6D (FIG. 2). As seen in FIGS. 1 and 3, each of the walls 6A–6D and the floor 4 of the housing 2 are provided with an inner wall member or partition 14 and an outer wall member or partition 16, the partitions 14,16 being spaced from each other. The space 18 between the partitions 14,16 preferably is left empty except for air, as shown in FIG. 3. Alternatively, the space may be filled with a sound absorption material 19, such as a polyurethane or polyethylene foam or glass fiber bats, as shown in a wall portion in FIG. 3 for illustrative purposes. As noted above, the inner and outer partitions 14, 16 are of a semi-rigid material having sufficient flexibility to provide a generally "soft" texture to the housing 2, but sufficient rigidity to maintain the integrity of the housing configuration. A material found suitable is polyethylene of a relatively low density. Such material provides the mechanical characteristics desired, and also provides good sound attenuation and isolation. However, housing 2 may be made of a high density polyethylene or some other suitable plastic material for other applications.

Referring to FIG. 3, it will be seen that the front wall 6C is substantially less in height than the back wall 6D. An upper edge surface 30 of each of the side walls 6A, 6B declines from the back wall 6D to the front wall 6C, as is best shown in FIG. 3. Accordingly, the door 8, when closed, declines from the back wall 6D to the front wall 6C, and the window pane 12 thereby faces not only upwardly, but also forwardly. This inclined portion of window pane 12 facilitates viewing of an infant in the crib from in front of the crib.

The door 8 includes a rectangular frame portion 32 having an inner partition or layer 34 and an outer partition or layer 36 (FIG. 3), which may be of the same material as the inner and outer layers 14, 16 of the walls of housing 2 and which are spaced apart to define a void 38 (FIG. 3) which may be empty or may be filled with a sound absorption material. The door frame portion 32 is provided with a groove 44 in which is disposed the window 12. Groove 44 is open to the exterior via an opening 42 (FIG. 3) in one side of door 8. In practice, the window pane 12 is inserted into the groove 44 via side opening 42 immediately after the door 4 is removed from a mold and while still hot. The door frame portion 32 thereafter cools and shrinks onto the window pane 12 so as to securely bond the window pane in place and effect a seal between it and door frame portion 32.

Figure 4:
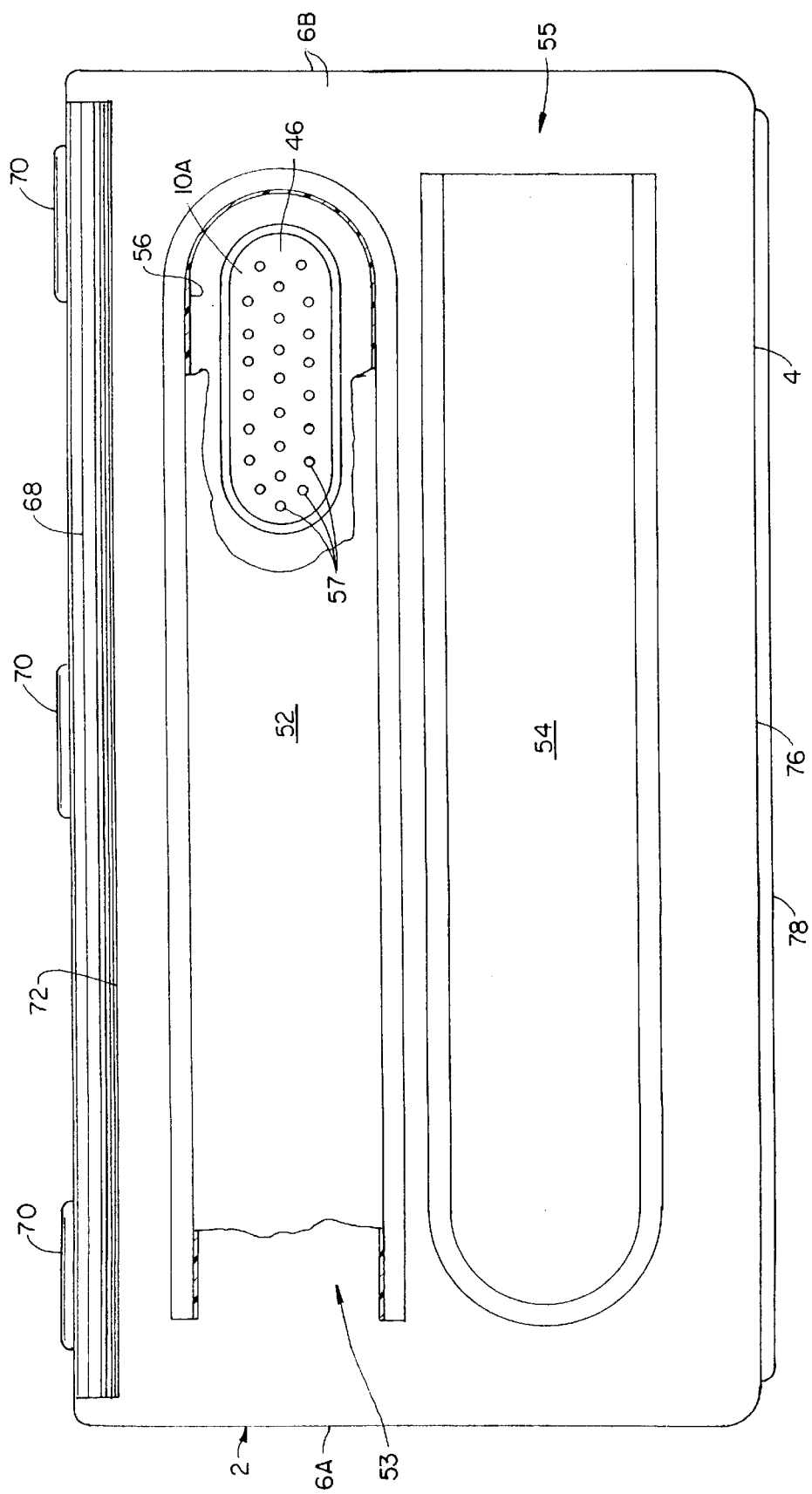
FIG. 4 is a rear elevational view, partly broken away, of the crib of FIG. 1.

Referring to FIGS. 2-4, it will be seen that the ventilation means 10 comprises an air inlet 10A and an air outlet 10B in the form of openings 57 extending through a selected one of the walls 6, preferably the back wall 6D as shown. Fixed to the outer wall 16 (FIGS. 1, 3 and 4) of back wall 6D is a first preformed air channel member 52 in communication with openings 57 of air inlet 10A, and a second preformed air channel member 54 in communication with the openings of air outlet 10B. Channel members 52 and 54 are open at their ends 53 and 55 respectively located away from air inlet 10A and air outlet 10B respectively. Fan means (not shown) may be connected to one or both of the channels to facilitate the inflow of fresh air and outflow of exhaust air. Channel members 52, 54 may be made of metal but preferably are made of an organic plastics material, e.g., the same material as housing 2 and door 8. Members 52,54 may be provided with liners 56 of sound-absorbing material (FIGS. 3 and 4).

Referring to FIGS. 1 and 3, it will be seen that preferably air inlet 10A and air outlet 10B each comprises a depression or recess 51 in inner partition 14 and an outer depression 46 in outer partition 16, with the bottoms of the recessed portions 51, 53 being contiguous with each other to form a double wall 48 through which extend holes 57. Thus, the "dead air" space between the inner and outer partitions of the rear wall are not compromised by the ventilation means 10.

The apparatus also is provided with means for introducing controlled acoustic signals from a source (not shown) outside of the crib to the infant in the crib, and for carrying signals from sensor means (not shown) mounted on the infant in the crib to instrumentation (not shown) outside of the crib. More specifically, as shown in FIG. 1, a conduit means 58 is provided in a selected one or more of the walls 6, such as side wall 6A, for retaining in an air-tight manner an acoustic signal transmission line T that is connected to the infant. The conduit means 58 comprises a conical recess 60 in the outer partition 16 of side wall 6A. Recess 60 is shaped so as to extend to the inner partition 14. An opening 64 is formed in partition 14 in line with recess 60 at the bottom of recess 60. An elastomeric grommet 66 is locked in place in recess 60 and opening 64 for effecting air-tight retention of the transmission line T where it passes through the grommet 66 and into the interior of the crib.

Referring to FIGS. 1, 2 and 4, it will be seen that the door 8, near its rearward edge 68, is provided with one or more protruding ribs 70. When the door 8 is closed, the ribs 70 are spaced from the upper edge 72 of back wall 6D. However, when door 8 is opened to the raised position shown in phantom in FIG. 3, the ribs 70 engage the upper edge 72 of the back wall, thereby acting as stops to support the door 8 in the open position shown in phantom in FIG. 3.

The inner partition 14 of the infant-supporting floor 4 provides an inner or upper surface 74 (FIG. 3), which serves to support bedding (not shown), and the prostrate infant. The outer partition 16 of the floor 4 provides an exterior bottom surface 76 for the crib. Legs 78, which may be in the form of elongated ridges, are integral with the outer partition 16 of floor 4 and extend therefrom to engage a supporting surface (not shown), such as a table top. Legs 78 serve to support and hold the crib with the floor 4 spaced from the supporting surface. Legs 78 are molded as integral parts of outer partition 16 and preferably are hollow so that their interiors 80 are in communication with the space 18 between the inner and outer partitions 14,16 of floor 4.

Referring again to FIGS. 1-3, it will be seen that the crib preferably is provided with two telescoping struts 82 connecting housing 2 and door 8. Preferably, each strut 82 includes a gas cylinder 84 (FIG. 3) and a telescoping rod 86 extending therefrom, the gas cylinder 84 being pivotally connected to a rigid mounting plate 88 fixed to the inner partition 14 of one of the side walls 6A and 6B, and the rod 86 being pivotally attached directly to the inner partition 34 of the door 8, or preferably to a rigid plate 89 fixed to that door partition. As shown in FIG. 3, the cylinder 84 of each strut is pivotally attached to mounting plate 88 at a pivot point 90. The latter is offset from the axis of the hinge pivot pins 92 for the door 8 and the pivot point 94 for the distal end of rod 86.

The arrangement of strut and door pivot points 90, 92, 94 enables the struts 82 to provide assistance in opening and closing the door 8. For example, it has been found in operation that when the door 8 is lifted about 20-30 degrees from its closed position, the struts urge the door to the fully open position and, thereafter, urge the door to remain open, along with the ribs 70. As the door 8 is lowered to its closed position, the struts provide a slight closing force when the door reaches the 5°-10° open position. Once the door is closed, the struts provide insufficient lifting force to cause the door to move up from its closed position without substantial manual assistance.

It has been found that cylinders 84 charged with nitrogen provide the beneficial opening and closing features described hereinabove. However, other devices may be used to provide similar opening and closing functions.

There is thus provided an audiometric booth which is suited for infants and in which infants may easily be placed and remain safe and comfortable during hearing examinations.

It is to be understood that the present invention is by no means limited to the particular construction herein disclosed and/or shown in the drawings, but also comprises any modifications or equivalents within the scope of the claims.

What is claimed is:

1. An audiometric crib for infants, said crib comprising:

a housing having a floor for supporting a prostrate infant, and front, back, and side walls upstanding from said floor;

a door connected to said housing and adapted to move between an open position for moving the infant into and out of said housing, and a closed position for isolating the infant from ambient noise and for conducting auditory tests on the infant;

ventilation means for passing air into said housing and exhausting air from said housing, said ventilation means comprising at least one air inlet and at least one air outlet in said back wall, a first air channel fixed to an outer surface of said back wall and in communication with said air inlet and a second air channel fixed to said outer surface of said back wall and in communication with said air outlet, and a liner of sound-absorbing material disposed in each of said air channels;

a window positioned in said crib such that the infant may be viewed from positions in front of said crib and over said crib.

2. A audiometric crib for infants, said crib comprising:

a housing made of a plastic material and having a floor for supporting a prostrate infant, and walls upstanding from said floor; said upstanding walls including front and back walls and first and second side walls, said front wall being substantially less in height than said back wall, and said side walls having an upper edge surface that declines from proximate said back wall to said front wall, said front wall, said back wall and said side walls forming an opening through which an infant may be moved into and out of said housing;

a door connected to said housing for closing off said opening, said door being adapted to move between an open position whereby an infant may be moved into and out of said housing via said opening and a closed position wherein said opening is closed off by said door so as to isolate an infant in said housing from ambient noise for the purpose of conducting auditory tests on the infant, said door comprising a frame portion having an inner wall and an outer wall, said inner and outer walls being spaced from each other and at an inner periphery thereof extending toward each other with a portion of each extending within a void defined by said inner and outer walls and toward an outer periphery of said frame to form an inner edge groove with parallel upper and lower walls comprising extensions of said outer and inner walls and a bottom wall connecting said upper and lower walls, and a transparent window pane mounted in said groove, said door and said transparent window pane when said door is in said closed position declining such that an infant in said crib may be viewed through said window pane from positions in front of said crib and over said crib; and ventilation means for passing air into said housing and exhausting air from said housing, said ventilation means comprising an air inlet and an air outlet communicating with the interior of said housing through recesses in said back wall, a first air channel fixed to an outer surface of said back wall in communication with said air inlet and a second air channel fixed to said outer surface of said back wall in communication with said air outlet.

* * * * *